United States Patent [19]

Mirviss

[11] Patent Number: 4,684,735

[45] Date of Patent: Aug. 4, 1987

[54] PROMOTION OF RANEY NICKEL HYDROGENATION CATALYST

[75] Inventor: Stanley B. Mirviss, Stamford, Conn.

[73] Assignee: Stauffer Chemical Company, Westport, Conn.

[21] Appl. No.: 749,971

[22] Filed: Jul. 1, 1985

[51] Int. Cl.$^4$ .......................................... C07D 233/72
[52] U.S. Cl. .................................. 548/308; 546/210; 548/309; 585/270; 585/276; 585/277
[58] Field of Search ................ 548/308, 309; 546/210; 585/276, 277, 270

[56] References Cited

U.S. PATENT DOCUMENTS 2,479,065  8/1949  Gresham ............................ 548/308

OTHER PUBLICATIONS

Bond, H., *J. Biol. Chem.*, 175, 531–4 (1948).
Chemical Abstracts, 88: 177763u (1978) [Matviichuk, A., et al., *Deposited Doc.* 1976, Viniti 1667-76].
Pizey, J., *Synthetic Reagents*, vol. II, Malsted Press, NY, 1974, pp. 180–181, 188–193 and 290.
Doyle, F., et al., *J. Chem. Soc.*, 1955, p. 2271.
Ward, H., *J. Am. Chem. Soc.*, 74, 4212 (1952).
Borrows, E., et al., *J. Chem. Soc.*, 1949, S185.
Levering, D., et al., *J. Am. Chem. Soc.*, 72, 1190 (1950).
Tucker, S., *J. Chem. Ed.* 1950, 489.
Dominguez, N., et al., *J. Org. Chem.*, 24, 1625 (1961).
Walter, L., et al., *J. Am. Chem. Soc.*, 63, 2772 (1941).
R. Augustine, *Catalytic Hydrogenation*, Marcel Dekker, Inc., New York, 1965, p. 32.
M. Freifelder, *Practical Catalytic Hydrogenation*, Wiley-Interscience, New York, 1971, pp. 32, 41, 44, 45, 46, 48, 52, 53, 84, 87, 91, 92, 94, 95 and 96.
L. Fieser et al., *Organic Chemistry*, 2nd ed., D. C. Heath, Boston, 1950, pp. 221–224.
P. Rylander, *Hydrogenation Methods*, Academic Press, London, 1985, p. 53.
Pauling, L., *The Nature of the Chemical Bond*, Cornell J. Press, Ithaca, 1960, p. 275.
Whitmore, F., *Organic Chemistry*, 2nd ed., D. Van Nostrand, New York, 1951, pp. 295 and 493.

*Primary Examiner*—Richard A. Schwartz
*Attorney, Agent, or Firm*—Paul J. Juettner

[57] ABSTRACT

There is disclosed a number of processes for the promotion of the Raney Nickel catalyzed hydrogenation of carbon-carbon double bonds. (a) One process uses tertiary amines to promote the Raney Nickel catalyzed hydrogenation. (b) Another process uses acetylene and acetylene derivatives to promote the Raney Nickel catalyzed hydrogenation. The promotion of Raney Nickel catalyst is particularly suited for the reduction of unsaturated hydantoins to saturated hydantoins and also for the reduction of cyclic and acyclic olefins and diolefins to the corresponding cyclic and acyclic alkanes.

10 Claims, No Drawings

PROMOTION OF RANEY NICKEL HYDROGENATION CATALYST

FIELD OF THE INVENTION

The present invention relates to improved processes for the promotion of Raney Nickel catalyzed hydrogenation, or reduction, of carbon-carbon double bond containing compounds.

BACKGROUND OF THE INVENTION

The reduction of carbon-carbon double bond containing compounds is a widely used chemical process having a large variety of applications. For instance, a desired alkane can be easily produced by reduction of the corresponding alkene.

One commonly employed technique for the reduction of these carbon-carbon double bonds is catalytic hydrogenation wherein a catalyst is employed to hydrogenate, or reduce, the double or olefinic bonds. Examples of catalysts which have been employed to reduce carbon-carbon double bonds include noble metal catalysts such as platinum or palladium. Other commonly employed catalysts include copper chromite, cobalt molybdate, and finely divided nickel or cobalt.

One of the most commonly used hydrogenation catalysts is Raney Nickel. While a somewhat effective hydrogenation catalyst, the Raney Nickel catalyst exhibits declining catalytic activity upon prolonged storage necessitating the use of either a freshly prepared or newly purchased catalyst for maximum catalytic activity. Since preparation or purchase of a new batch of Raney Nickel can be expensive, an alternative procedure for ensuring maximum catalytic activity is to use a promoting agent. Various promoting agents for Raney Nickel catalyzed hydrogenation are known.

In Pizey, *Synthetic Reagents*, Volume II, John Wiley and Sons, it is reported that the addition of organic bases to a Raney Nickel catalyst results in retardation of the hydrogenation of ketones, with the use of low concentrations of triethylamine and N,N-dimethylaniline being exceptions to the above rule. It is also reported in the above reference that triethylamine retards hydrogenation of the carbon-carbon double bond in alpha, beta unsaturated ketones while increasing hydrogenation of the keto group.

In order to ensure maximum efficiency, an effective promoting agent for the Raney Nickel catalyzed hydrogenation of carbon-carbon double bonds is needed.

SUMMARY OF THE INVENTION

In accordance with the present invention, there are disclosed a number of processes for the promotion of Raney Nickel catalyzed hydrogenation of aliphatic carbon-carbon double bonds. One embodiment of the present invention comprises the addition of a tertiary amine as a promoting agent. Another embodiment of the present invention comprises the use of acetylenic compounds as promoting agents.

DETAILED DESCRIPTION OF THE INVENTION

The present invention is directed to the promotion of the Raney Nickel catalyzed hydrogenation of carbon-carbon double bonds. While the processes of the present invention may be used for the promotion of the Raney Nickel catalyzed hydrogenation of carbon-carbon double bonds in any aliphatic compound containing said bonds, they are particularly suited for the promotion of the Raney Nickel catalyzed hydrogenation, or reduction, of unsaturated hydantoins to saturated hydantoins. The remainder of the application will be discussed in relation to the reduction of unsaturated hydantoins although it is to be understood that the processes of the present invention are equally applicable to the promotion of Raney Nickel catalyzed hydrogenation of carbon-carbon double bonds in a wide variety of compounds, for example, dienes and cyclic dienes. Generally, the compounds which can be reduced by the process of the present invention are those which contain aliphatic carbon-carbon double bonds, i.e., non-aromatic compounds. These compounds include the aforementioned cyclic and acyclic dienes as well as cyclic and acyclic compounds containing one double bond. Hereinafter the term "compound containing an aliphatic carbon-carbon double bond" refers to the above mentioned non-aromatic compounds.

The process of the invention is particularly suited for the promotion of the Raney Nickel catalyzed reduction of substituted unsaturated hydantoins of the general formula.

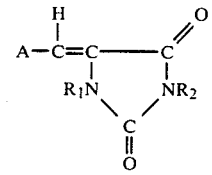

where A is X or Y, and X is an unbranched or branched alkyl or alkenyl group, a cycloalkyl group, a cycloalkenyl group, an alkylthio group, a haloalkyl group, a haloalkenyl group, a hydroxyalkyl group, an aralkyl group, a mono- or dialkylaminoalkyl group, an acylaminoalkyl group, or a mercaptoalkyl group. Preferably the alkyl groups contain 1 to about 20, especially 1 to about 10 carbon atoms, the alkenyl groups 2 to about 10, especially 2 to about 5 carbon atoms, the cycloalkyl and cycloalkenyl groups from about 3 to about 15, preferably from about 3 to about 10 carbon atoms. In a given case in the cycloalkyl or cycloalkenyl group, one or more —$CH_2$- units can also be replaced by —O—, 15, preferably from about 3 to about 10 ring atoms. The alkoxy, alkylthio, hydroxyalkyl, mercaptoalkyl, mono or dialkylaminoalkyl and acylaminoalkyl groups contain preferably 1 to about 10, especially 1 to about 6 carbon atoms in the alkyl or acyl groups, and

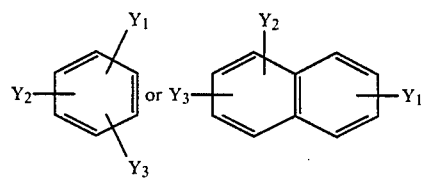

in which $Y_1$, $Y_2$, and $Y_3$ are the same or different and can be X as defined above, hydrogen, halogen, e.g. of atomic weight 9 to 80, a hydroxy group, a nitro group, a cyano group, an amino group, an aralkyl group, or an alkaryl group. Preferably, the aralkyl and the alkaryl groups contain from about 7 to about 15 carbons in the alkylene or alkyl groups. In a given case, two of the groups $Y_1$ to $Y_3$ together can form an alkylene or alkenylene group with from about 3 to about 5 carbon atoms whereby in this case one or more —OH$_2$— units can be replaced by —O—, —S—, or —NH— or —OH= can be replaced by —N=.

R$_1$ and R$_2$ are the same or different and are hydrogen, alkyl, aryl, or amino.

The unsaturated hydantoin to be reduced can be purchased commercially or can be synthesized, for example, through the condensation reaction of an aliphatic or aromatic aldehyde with a substituted or unsubstituted hydantoin.

One such condensation reaction is disclosed in U.S. copending application Ser. No. 641,888, now U.S. Pat. No. 4,582,903, entitled "New Inexpensive Catalyst for the Production of Unsaturated Hydantoins", in which the condensation reaction of an aldehyde and hydantoin is carried out in the presence of a basic salt of an inorganic acid. In this process, representative aldehydes which may be used include, but are not limited to, aliphatic aldehydes such as butyraldehyde, isobutyraldehyde, valeraldehyde, isovaleraldehyde, caproaldehyde, enanthaldehyde, nonaldehyde, cyclobutylaldehyde, cyclopentylaldehyde, cyclohexylaldehyde, furfural, 2-thiophenealdehyde, 2-pyrrolealdehyde, imidazolealdehyde, oxazolealdehyde, 3-indolealdehyde, pyridylaldehyde, pyrimidylaldehyde, malonic acid half aldehyde, as well as the monoaldehyde derivatives of dicarboxylic acids such as, for example, succinic, oxalic, glutaric and adipic acid.

Aromatic aldehydes can also be used. Examples of aromatic aldehydes include, but are not limited to, benzaldehyde, tolylaldehyde, 4-isopropylbenzaldehyde, 4-hydroxybenzaldehyde, 8,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicylaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde. Additional aldehydes include p-tolylaldehyde, m-tolylaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 8-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridinebenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzaldehyde, 2-propoxybenzaldehyde, 3-exthoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acetylthiobenzaldehyde, 4-propionoxybenzaldehyde, 4-formoxybenzaldehyde, 4-butyroxybenzaldehyde, 8,4-tetramethylenebenzaldehyde, 3,4-trimethylenebenzaldehyde, 3,4-dihyroxybenzaldehyde, alphanaphthaldehyde, betanaphthaldehyde, and 3-indenecarboxaldehyde.

In addition, the above process is also suited to the condensation reaction of hydantoins substituted at the N-1 and N-3 position such as 3-methylhydantoin, 1,3-diacetylhydantoin, 1,3-diphenylhydantoin, 3-benzylhydantoin, 1,3-dibenzylhydantoin and the like.

It has now been discovered that the unsaturated hydantoin produced in the above reaction, available commercially or produced through other means, can be reduced in a fast reaction time to the corresponding saturated hydantoin by carrying out the hydrogenation step using Raney Nickel catalyst in the presence of a promoting agent to increase the hydrogenation rate.

The Raney Nickel catalyst employed is available commercially (for example, from the Davison Division of W. R. Grace). Briefly, the preparation of this catalyst involves fusing about 50 parts nickel with about 50 parts aluminum as described in U.S. Pat. Nos. 1,628,190 and 1,915,473, pulverizing the alloy and dissolving out most of the aluminum with sodium hydroxide solution [J. Am. Chem. Soc. 54, 4116 (1932)]. The nickel is then washed to remove any residual sodium hydroxide [Ind. and Eng. Chem. 33 1199 (1940)]. The exact mechanism through which Raney Nickel exerts its catalytic activity is not known. Various theories have been put forth including absorbed hydrogen or the formation of a nickel hydride. A complete discussion of this subject can be found in Freifelder, *Practical Catalytic Hydrogenation*, Wiley Interscience, 1971 pp. 6–7, the discussion therein being incorporated by reference. As is known to those skilled in the art, the Raney Nickel catalyst must be kept under water. The Raney Nickel catalyst produced through the above procedure will hereinafter be referred to as a "nickel catalyst".

An example of the Raney Nickel catalyzed hydrogenation of unsaturated hydantoins to saturated hydantoins is disclosed in copending U.S. application Ser. No. 641,886, now abandoned, entitled "Reduction of Unsaturated, Substituted Hydantoins to Saturated, Substituted Hydantoins" filed Aug. 17, 1984, the material therein being incorporated by reference. While the above application discloses the reduction of unsaturated hydantoins by using Raney Nickel catalyst in the presence of more than a stoichiometric amount of caustic, the present invention is directed to the promotion of Raney Nickel catalyzed hydrogenation of carbon-carbon double bonds under a wide variety of reaction conditions, including in the presence of stoichiometric or less than stoichiometric amounts of caustic.

In one embodiment of the present invention, it has now surprisingly been discovered that the Raney Nickel catalyzed hydrogenation of carbon-carbon double bonds is promoted in the presence of a tertiary amine. This result is rather surprising in light of the literature which reports that the presence of the tertiary amine actually retards hydrogenation of the carbon-carbon double bond.

The tertiary amines which can be employed as promoting agents in the present invention are those corresponding to the general formula

N(R)$_3$ wherein R is C$_1$ to C$_{12}$ straight or branched chain alkyl, aryl, substituted aryl, alkaryl, substituted alkaryl, aralkyl and substituted aralkyl. Suitable amines will have some degree of solubility in the hydrogenation media.

Examples of tertiary amines which can be used as promoting agents in the present invention include, for example, triethylamine, trimethylamine, tripropylamine, triisobutylamine, tricyclohexylamine, dimethylcyclohexylamine, N,N-dimethylaniline, N-methyl-N-ethylaniline, and the like. Combinations of the above amines can also be used. However, it is preferred to use tertiary alkyl amines with at least some degree, i.e., partial solubility in the hydrogenation medium.

The amount of tertiary amine used as a promoting agent can range from about 0.10 to about 50 weight percent, preferably from about 0.5 to about 25 weight percent based on the amount of Raney Nickel. In the case of the promotion of the Raney Nickel catalyzed reduction of unsaturated hydantoins, the tertiary amine can be used at a level ranging from about 0.01 to about 20 weight percent, preferably from about 0.05 to about 10 weight percent based on the unsaturated hydantoin.

It has also surprisingly been found that tertiary amines function as efficient promoting agents for different grades (types) of Raney Nickel catalyst. Thus, consistent hydrogenation of carbon-carbon double bonds can be achieved through the use of any Raney Nickel catalyst plus the promoting agent.

The media in which the hydrogenation reaction is conducted is dependent upon the particular carbon-carbon double bond containing compound which is to be reduced. For instance, if the carbon-carbon double bond containing compound to be reduced is an unsaturated hydantoin, the Raney Nickel catalyst and tertiary amine can be added to an aqueous alkaline media. Organic solvents and especially alcohols can also be used alone or in combination with other solvents and/or water.

Since the tertiary amine is functioning as a promoting agent, it can be added at any time to the reaction medium although it is preferable that the tertiary amine promoting agent be present at the start of the reaction with the Raney Nickel.

The hydrogenation reaction in the presence of the promoting agent can be carried out at atmospheric pressure. If faster reaction times are desired, elevated pressures ranging from about 0.25 to about 200 atmospheres may be used.

The temperature at which the hydrogenation reaction is carried out is preferably from about room temperature (25° C.) to about 58° C. If desired, temperatures ranging from about 0° C. to about 150° C. can also be used. In the case of the Raney Nickel catalyzed hydrogenation of unsaturated hydantoins, particularly 5-alkenyl hydantoins, it is preferred to keep the temperature below 60° C. to avoid hydrolysis of the unsaturated hydantoins to the corresponding pyruvic acid or salt thereof. Such hydrolysis can occur to a degree at reaction temperatures of 60° C. or higher and particularly in the presence of caustic.

In another embodiment of the present invention, it has also been found that acetylenes and acetylenic compounds function as efficient promoting agents for the Raney Nickel catalyzed hydrogenation of carbon-carbon double bonds.

The acetylene, or acetylenic compounds which are useful promoting agents in the present invention are those corresponding to the formula

wherein R and $R_1$ are the same or different and are $C_1$ to $C_{10}$ straight or branched chain substituted or unsubstituted alkyl, substituted or unsubstituted cycloalkyl, substituted unsubstituted cycloalkenyl, substituted or unsubstituted alkaryl or aryl or substituted aryl up to three fused rings, substituted or unsubstituted cycloalkyl or cycloalkenyl groups wherein one or more of the —$CH_2$— units is replaced by —O—, —S— or —NH— or —C≡ is replaced by —N— so that there is present the corresponding heterocyclic ring with 3 to about 15 carbon atoms. By "unsubstituted" as used herein is meant the parent compound, i.e., benzene, pyridine, etc. By "substituted" as used herein is meant any substituent which is non-reactive under the reaction conditions employed. Examples of such substituents include, but are not limited to, amino, thio, alkoxy, sulfono, amido, hydroxy, alkyamino, aminoalkyl, alkylthio and the like.

Since the presence of the carbon-carbon triple bond is the important factor which theoreticially imbues the promoting properties upon the acetylenic compounds, it is also within the scope of the present invention to use as promoting agents compounds containing more than one carbon-carbon triple bond. Hereinafter, the term "acetylenic compound" refers to the parent compound, acetylene, as well as derivatives thereof, e.g., phenylacetylene, tolylacetylene, 1,7-octadiyne, and hexynes-1 and -2. Preferably, the acetylenic compound will have some degree of solubility in the hydrogenation medium.

The reaction conditions employed when using acetylenic compounds as promoting agents for the Raney Nickel catalyzed hydrogenation of carbon-carbon double bonds are essentially similar to those employed when a tertiary amine is used as a promoting agent. Thus, the temperature, pressure and medium conditions under which the reaction is conducted are those hereinbefore described. Similarly, acetylnic compounds with at last partial solubility also act as promoting agents for different grades (types) of Raney Nickel.

The amount of acetylenic compound employed as a promoting agent can range from about 0.10 to about 50 weight percent preferably from about 0.5 to about 25 weight percent based upon the amount of Raney Nickel used. If the acetylenic compound is used as a promoting agent for the Raney Nickel catalyzed hydrogenation of unsaturated hydantoins, the amount of acetylenic compound used can range from about 0.10 io to about 50 weight percent based on the amount of Raney Nickel needed to reduce the unsaturated hydantoin.

The present invention is illustrated by the following Examples.

COMPARATIVE EXAMPLE 1

A 500 milliliter, round bottomed, 3 necked flask was fitted with a mechanical stirrer, thermometer, dip tube for hydrogen or nitrogen flow, heating mantle and condenser. The flask was preflushed with nitrogen and then 30 grams (0.15 mole) of benzalhydantoin, 270 grams of deoxygenated distilled water, and 6.5 grams (0.16 mole) of sodium hydroxide were added. Under a nitrogen purge, 3 grams of 50% No. 2800 Raney Nickel (Davison Division of W. R. Grace) in water (1.5 gram dry basis or 5 wt. % (dry basis) based on benzalhydantoin) were added. Under atmospheric pressure, the hydrogen flow was turned on, the reaction mixture was vigorously stirred and the temperature was raised to 50° C. and held throughout the reaction. Samples were periodically withdrawn and submitted for liquid chromatographic analysis. The hydrogenation reaction was 85% complete in 83 hours, 96% complete in 48.5 hours and 100% complete in 56.5 hours. A subsequent repeat run required 56 hours for 83% completion and 71 hours for 100% completion.

EXAMPLE 1

The procedure was essentially that of Comparative Example 1 except 2 drops of triethylamine were added at the start of the reaction. The hydrogenation was 85% complete in 20 hours, 97% complete in 27.5 hours and 100% complete in 35 hours.

COMPARATIVE EXAMPLE 2

The procedure was that of Comparative Example 1 except 3 grams of No. 200 Raney Nickel (Davison Division of W. R. Grace) were used. The hydrogenation was 87% complete in 35 hours, 92% complete in 66 hours and 100% complete in 74 hours.

EXAMPLE 2

The procedure was that of Comparative Example 2 except 2 drops of triethylamine were added at the beginning of the reaction. The hydrogenation was 81% complete in 26 hours, 91% complete in 33 hours and 100% complete in 40 hours.

COMPARATIVE EXAMPLE 3

The procedure was essentially that of Comparative Example 1 except 3 grams of No. 2400 Raney Nickel (Davison Division of W. R. Grace) were used. The hydrogenation was 75% complete in 19 hours, 89% complete in 42 hours and 100% complete in 57 hours.

EXAMPLE 3

The procedure was essentially that of Comparative Example 3 except 2 drops of triethylamine were added at the beginning of the reaction. The hydrogenation was 84% complete in 18 hours, 92% complete in 24 hours and 100% complete in 33 hours.

COMPARATIVE EXAMPLE 4

This Example shows the need for a soluble tertiary amine. Instead of using 2 drops of triethylamine as in Examples 1 to 3, 3 grams of poly(vinylpyridine) were used with the No 2400 Raney Nickel. The hydrogenation was 75% complete in 19 hours, 89% complete in 42 hours and 100% complete in 57 hours.

EXAMPLE 4

The catalyst from Example 3 (No. 2400 Raney Nickel (Davison Division of W. R. Grace)) was recycled and used with 2 drops of triethylamine. The hydrogenation results were exactly those seen in Example 3, i.e., 100% complete in 33.5 hours.

EXAMPLE 5

Similar to Example 8 except the reaction was run at 10 psig hydrogen pressure and with better agitation. Oomplete hydrogenation was seen in 11 hours.

The following Examples illustrate the reduction of dodecene-1:

COMPARATIVE EXAMPLE 5

To a well stirred reactor was added 25 g. of dodecene-1 in 100 ml. of methyl alcohol and under an atmosphere of nitrogen, 1.5 g. of NaOH and 3 g. of 50% No. 2800 Raney Nickel in water (1.5 g. dry basis) (from Davison) and 3 g. of 50% No. 2400 Raney Nickel (from Davison) (1.5 g. dry basis) were added. With vigorous stirring at 40–45° C., hydrogen was bubbled in at atmospheric pressure. The reaction was periodically monitored by GC analysis. After 2 hrs. the hydrogenation was 61% complete. The hydrogenation was 100% complete in about 4 hrs.

EXAMPLE 6

This reaction was carried out identical to Comparative Example 5 except that 0.4 g. of triethylamine was also included. The reaction was 69% complete in 2 hrs. and was 100% done in 3.25 hrs.

The following Examples illustrate the reduction of dicyclopentadiene:

COMPARATIVE EXAMPLE 6 a. With 40 wt. % Raney Nickel

A well stirred reaction vessel was charged with 25 g. of dicyclopentadiene and 100 ml. of methanol. Under nitrogen was added 3 g. of NaOH and then 10 g. of 50% No. 2400 Raney Nickel (from Davison) in water (5 g. dry basis) and 10 g. of 50% No. 2800 Raney Nickel (from Davison) in water (5 g. dry basis). With good stirring at 50° C., hydrogen was bubbled in at atmospheric pressure. The hydrogenation was sampled periodically for GC analysis After 2.5 hrs., the reaction was 52% complete and the reaction was 100% complete in 4.5–4.75 hrs.

EXAMPLE 7

The same reaction as in Comparative Example 6 above was done with 1 g. of triethylamine also present. The reaction was 59% complete in 2.5 hrs. and was 100% complete in 3.75 hrs.

COMPARATIVE EXAMPLE 7 b. With 16 wt. % Raney Nickel

The same reaction as in Comparative Example 6 above was carried out except that 4 g. of 50% No. 2800 (2 g. dry basis), and 4 g. of 50% No. 2400 (2 g. dry basis) Raney Nickels (from Davison) were used. The reaction was 63% complete in 4 hrs. and 100% in 6 hrs.

EXAMPLE 8

The same reaction as in Comparative Example 7 above was carried out except that 0.4 g. of triethylamine was also used. The reaction was 72% complete in 4 hrs. and 100% complete in 5–5.25 hrs.

The following proposed Examples illustrate that the tertiary amine promotion of the Raney Nickel catalyzed reduction of carbon-carbon double bond containing compounds can be extended to other unsaturated compounds.

PROPOSED EXAMPLE 1

By essentially following the procedure of Examples 1 to 8 the nickel catalyzed reduction of an unsaturated alcohol containing at least one aliphatic carbon-carbon double bond is promoted in the presence of a tertiary amine.

PROPOSED EXAMPLE 2

By essentially following the procedures of Examples 1 to 8, the nickel catalyzed reduction of an alpha, beta, or other unsaturated carboxylic acids or esters containing at least one aliphatic carbon-carbon double bond is promoted in the presence of a tertiary amine.

EXAMPLE 9

This Example shows the use of an acetylenic compound as a promoting agent. The procedure was that of Comparative Example 1 except 2 drops of phenylacetylene (0.3 wt. % based on benzalhydantion) were added at the beginning of the reaction. The hydrogenation was 92% complete in 85 hours and 100 % complete in 43 hours.

PROPOSED EXAMPLE 3

By essentially following the procedure of Example 9 and substituting therein compounds containing aliphatic carbon-carbon double bonds such as dicyclopentadiene, 1-dodecene, unsaturated alcohols or unsaturated carbonyl-containing compounds as enumerated in Proposed Example 2, the nickel catalyzed reduction of these compound containing at least one aliphatic carbon-carbon double bond is promoted in the presence of an acetylenic compound.

Additional features of the preferred and most preferred embodiments of the present invention are found in the claims hereinafter.

What is claimed is:

1. A process for the promotion of the nickel catalyzed reduction of unsaturated hydantoin compounds containing at least one exocyclic aliphatic carbon-carbon double bond of the formula:

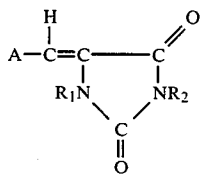

wherein A is X or Y and X is unbranched or branched alkyl or alkenyl, cycloalkyl, cycloalkenyl, alkylthio, hydroxyalkyl, aralkyl, mono or dialkylalkylaminoalkyl, acylaminoalkyl, mercaptoalkyl, cycloalkyl having a —CH$_2$— group replaced by —O—, —S—, or —NH— cycloalkenyl having a —CH= replaced by —O—, —S—, or —N=; and Y is

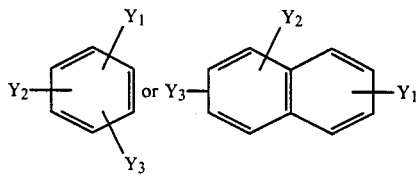

wherein $Y_1$, $Y_2$ and $Y_3$ are the same or different and are hydrogen, alkyl, alkenyl, cycloalkyl, cycloalkenyl, aryl, halogen, hydroxy, nitro, cyano, amino, alkylaminoalkyl, dialkylaminoalkyl, alkoxy, alkylthio, acyloxy, mercaptoalkyl, alkaryl, aralkyl, acylaminoalkyl, cycloalkyl having a —CH$_2$— group replaced by —O—, —S—, or —NH— cycloalkenyl having a —CH= replaced by —N= or where two of the members, $Y_1$, $Y_2$, and $Y_3$ are joined together to form an alkylene group having at least one —CH$_2$— group replaced by —O—, —S—, or —NH— or an alkenylene group having at least one —CH= group replaced by —N=; and $R_1$ and $R_2$ are the same or different and are hydrogen, alkyl, aryl, acyl or amino which consists essentially of using a teritiary alkyl amine as a promoting agent, the reduced compound having the formula

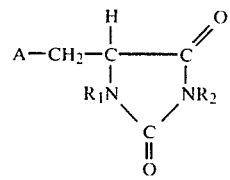

wherein A, R1, and R2 are as defined hereinbefore.

2. A process according to claim 1 wherein the tertiary amine is triethylamine.

3. A process according to claim 1 wherein the unsaturated hydantoin is 5-benzalhydantoin.

4. The process as recited in claim 1 wherein the reduction is conducted in an aqueous alkaline medium.

5. The process as recited in claim 1 wherein the reduction is carried out in the presence of caustic.

6. A process for the promotion of the nickel catalyzed hydrogenation compounds containing at least one aliphatic carbon-carbon double bond which comprises using an acetylenic compound as a promoting agent.

7. A process according to claim 6 wherein the acetylenic compound is phenylacetylene.

8. A process according to claim 6 wherein the compound containing at least one aliphatic carbon-carbon double bond is an unsaturated hydantoin of the formula:

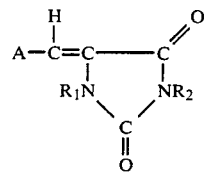

wherein A is X and X is unbranched or branched alkyl or alkenyl, cycloalkyl, cycloalkenyl, alkylthio, hydroxyalkyl aralkyl, mono or dialkyalkylaminolkyl acylaminoalkyl, mercaptoalkyl, cycloalkyl having a —CH$_2$ group replaced by —O—, —S—, or —NH—, cycloalkenyl having a —CH= replaced by —O—, —S—, or —N—;

$R_1$ and $R_2$ are the same or different and are hydrogen, alkyl, aryl, acyl or amino.

9. A process according to claim 6 wherein the compound containing at least one aliphatic carbon-carbon double bond is an unsaturated hydantoin of the formula:

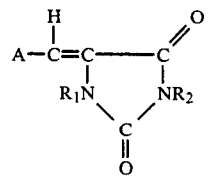

wherein A is Y and Y is

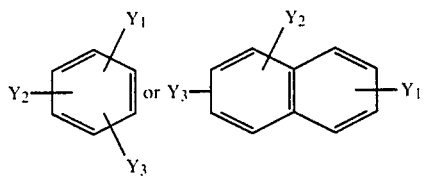

wherein $Y_1$, $Y_2$ and $Y_3$ are the same or different and are hydrogen, alkyl, alkenyl, cycloalkyl, cycloalkenyl, aryl, halogen, hydroxy, nitro, cyano, amino, alkylaminoalkyl, dialkylaminoalkyl, alkoxy, alkylthio, acyloxy, mercaptoalkyl, alkaryl, aralkyl, acylaminoalkyl, cycloalkyl having a —$CH_2$— group replaced by —O—, —S—, or —NH— cycloalkenyl having a —CH= replaced by —N— or where two of the members, $Y_1$, $Y_2$, and $Y_3$ are joined together to form an alkylene group having at least one —$CH_2$— group replaced by —O—, —S—, or —NH= or an alkenylene group having a —CH= group replaced by —N=;

$R_1$ and $R_2$ are the same or different and are hydrogen, alkyl, aryl, acyl or amino.

10. The process of claim 9 wherein the unsaturated hydantoin is 5-benzalhydantoin.

* * * * *

UNITED STATES PATENT AND TRADEMARK OFFICE
CERTIFICATE OF CORRECTION

PATENT NO. : 4,684,735

DATED : Aug. 4, 1987

INVENTOR(S) : Stanley B. Mirviss

It is certified that error appears in the above—identified patent and that said Letters Patent is hereby corrected as shown below:

Col. 2, line 46, "$-OH_2-$" should be "$-CH_2-$";

Col. 3, line 2, "$-OH_2-$" should be $-CH_2-$";

Col. 3, line 3, "$-OH=$" should be "$-CH=$";

Col. 3, line 33, "8,4,5-trimethoxybenzaldehyde" should be "3,4,5-trimethoxybenzaldehyde";

Col. 3, line 47, "8-nitrobenzaldehyde" should be "3-nitrobenzaldehyde";

Col. 3, line 67, "8,4-tetramethylenebenzaldehyde" should be "3,4-tetramethylenebenzaldehyde";

Col. 6, line 36, "last" should be "least";

Col. 6, line 45, "io" between "0.10" and "to" should be removed;

Col. 6, last line, "83 hours" should be "33 hours";

Col. 7, line 56, "Example 8" should be "Example 3";

Col. 7, line 58, "Oomplete" should be "Complete";

Col. 9, line 8, "85 hours" should be "35 hours";

Col. 9, line 41, "dialkylalkylaminoalkyl" should be "dialkylaminoalkyl";

Col. 10, line 13, "R1 and R2" should be "$R_1$ and $R_2$";

Col. 10, line 46, "dialkylalkylaminolkyl" should be "dialkylaminoalkyl";

Col. 10, line 47, "$-CH_2$" should be "$-CH_2-$";

Col. 10, line 51, "$-N-$" should be "$-N=$ and";

Col. 12, line 2, "$-NH-$" should be "$-NH-,$";

Col. 12, line 3, "$-N-$ or" should be "$-N=$ or";

UNITED STATES PATENT AND TRADEMARK OFFICE
CERTIFICATE OF CORRECTION

PATENT NO. : 4,684,735
DATED : Aug. 4, 1987
INVENTOR(S) : Stanley B. Mirviss

It is certified that error appears in the above—identified patent and that said Letters Patent is hereby corrected as shown below:

Col. 12, line 7, "-NH=" should be "-NH-";

Col. 12, line 8, "-N=" should be "-N=; and".

Signed and Sealed this

Seventeenth Day of May, 1988

Attest:

DONALD J. QUIGG

Attesting Officer

Commissioner of Patents and Trademarks